US00PP16897P2

(12) United States Plant Patent
Schoenmakers

(10) Patent No.: US PP16,897 P2
(45) Date of Patent: Jul. 25, 2006

(54) ***FITTONIA* PLANT NAMED 'FOREST FLAME'**

(50) Latin Name: *Fittonia verschaffeltii*
Varietal Denomination: Forest Flame

(75) Inventor: Kees Schoenmakers, Haaren (NL)

(73) Assignee: Schoenmakers Tropische Potcultures, Haaren (NL)

( * ) Notice: Subject to any disclaimer, the term of this patent is extended or adjusted under 35 U.S.C. 154(b) by 5 days.

(21) Appl. No.: 11/166,648

(22) Filed: Jun. 25, 2005

(51) Int. Cl.
*A01H 5/00* (2006.01)

(52) U.S. Cl. ..... Plt./373

(58) Field of Classification Search ..... Plt./373
See application file for complete search history.

(56) References Cited

PUBLICATIONS http://www.cpvo.edu.int/module_tech/rights_granted. ph p?SPECIEID=FIT02 . . . .*
http://www.rentokil–initial.com/press/item.php?id=227& PHPSESSID=a95785dd8c1c4425c6f . . . .*

* cited by examiner

*Primary Examiner*—Kent Bell
*Assistant Examiner*—W. C. Haas
(74) *Attorney, Agent, or Firm*—Mark P. Bourgeois

(57) ABSTRACT

A new cultivar of *Fittonia* plant named 'Forest Flame' that is characterized by small green leaves with red veins.

1 Drawing Sheet

Botanical classification: *Fittonia verschaffeltii.*
Variety denomination: 'Forest Flame'.

BACKGROUND OF THE INVENTION

The present invention relates to a new and distinct cultivar of *Fittonia* plant botanically known as *Fittonia verschaffeltii* and hereinafter referred to by the cultivar name 'Forest Flame'.

The new cultivar was discovered by the inventor in a cultivated area of Haaren, The Netherlands in 2002. 'Forest Flame' was discovered as a naturally occurring whole plant mutation of *Fittonia verschaffeltii* 'Josan' (not patented).

Asexual reproduction by terminal cuttings of the new cultivar 'Forest Flame' was first done in 2002 in Haaren, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Fittonia* cultivar 'Forest Flame'.

1. *Fittonia* 'Forest Flame' exhibits green leaves with red veins.
2. *Fittonia* 'Forest Flame' exhibits small leaves.

The closest comparison cultivar is the parent *Fittonia* 'Josan'. The new cultivar 'Forest Flame' is distinguishable from 'Josan' by the following characteristics:

1. 'Forest Flame' has a more compact habit than 'Josan'.
2. 'Forest Flame' has leaf margins that are wavier than 'Josan'.

BRIEF DESCRIPTION OF THE DRAWING

The accompanying photograph illustrates the distinguishing traits of *Fittonia* 'Forest Flame'. The plant in the photograph shows an overall view of a 12 week old plant.

The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Fittonia* cultivar named 'Forest Flame'. Data was collected in Haaren, The Netherlands from 12 week old greenhouse grown plants in 8.5 cm. containers. The time of year was Spring and the average temperature was 24 degrees Centigrade during the day and 22 degrees Centigrade at night. No photoperiodic treatments were used. Color determinations are in accordance with The Royal Horticultural Society Colour Chart 2001 edition, except where general color terms of ordinary dictionary significance are used. The growing requirements are similar to the species. 'Forest Flame' has not been tested under all possible conditions and phenotypic differences may be observed with variations in environmental, climatic, and cultural conditions, however, without any variance in genotype.

Botanical classification: *Fittonia verschaffeltii* 'Forest Flame'.
Use: Ornamental.
Parentage: 'Forest Flame' is a naturally occurring whole plant mutation of *Fittonia* 'Josan'.
Vigor: Moderate.
Growth rate: Moderate.
Growth habit: Broad spreading, upright.
Plant shape: Flattened globose.
Suitable container size: 8.5 cm. diameter container.
Height: Average 4.5 cm.
Width: Average 7.9 cm.
Hardiness: USDA Zone 10.
Propagation: Terminal cuttings.
Time to initiate roots: Approximately 21 days to produce roots on an initial cutting at 24 degrees Centigrade.

Time to produce a rooted cutting: Approximately 35 days to produce a rooted cutting at 24 degrees Centigrade.
Crop time: 12 weeks.
Root system: Fine and fibrous.
Stem:
*Branching habit.*—Freely branching.
*Average number of lateral branches.*—4.
*Pinching.*—No.
*Lateral branch diameter.*—2.0 mm. in diameter.
*Lateral branch length.*—2.9 cm. in length.
*Lateral branch strength.*—Moderately strong.
*Stem color.*—183A with internodes 144A.
*Pubescence.*—Dense, length 0.4 mm., color N155A.
*Internode length.*—1.4 cm. between nodes.
*Shape.*—Round.
*Surface.*—Dull.
*Stem strength.*—Moderately strong.
Foliage:
*Leaf arrangement.*—Opposite.
*Compound or single.*—Single.
*Leaf shape.*—Narrow elliptic.
*Leaf apex.*—Broad acute to rounded.
*Leaf base.*—Attenuate.
*Leaf texture.*—Glabrous, slightly rugose.
*Leaf length.*—Average 3.8 cm. in length.
*Leaf width.*—1.4 mm. in width.
*Quantity of leaves per lateral branch.*—Average 4.
*Pubescence.*—Short hairs on margins and undersides, 0.5 mm. in length, N155A.
*Leaf margin.*—Entire, considerably wavy.
*Vein pattern.*—Pinnate.
*Young leaf color,* (*upper surface*).—50A to 50B with small spots, 144A. Margins colored 139A.
*Young leaf color,* (*lower surface*).—195B with small dots, 137B. Margins colored 137A.
*Mature leaf color,* (*upper surface*).—Between 139A and 147A.
*Mature leaf color,* (*lower surface*).—146A to 146B, margins 147A.
*Vein color* (*lower surface*).—145B to 145C, base 177C.
*Vein color* (*upper surface*).—53C, darker toward leaf margins 53B, main vein 185A toward the base.
*Leaf attachment.*—Petiolate.
*Petiole dimensions.*—Average 6 mm. in length, 2 mm. in diameter, 1 mm. in height.
*Petiole color.*—185A, lower surface 177C.
*Durability of foliage to stress.*—High.
Flowers: Flowers have not been observed.
Disease and insect resistance: Plants of the new *Fittonia* have not been observed for disease or insect resistance.

It is claimed:

1. A new and distinct variety of *Fittonia* plant named 'Forest Flame' as described and illustrated.

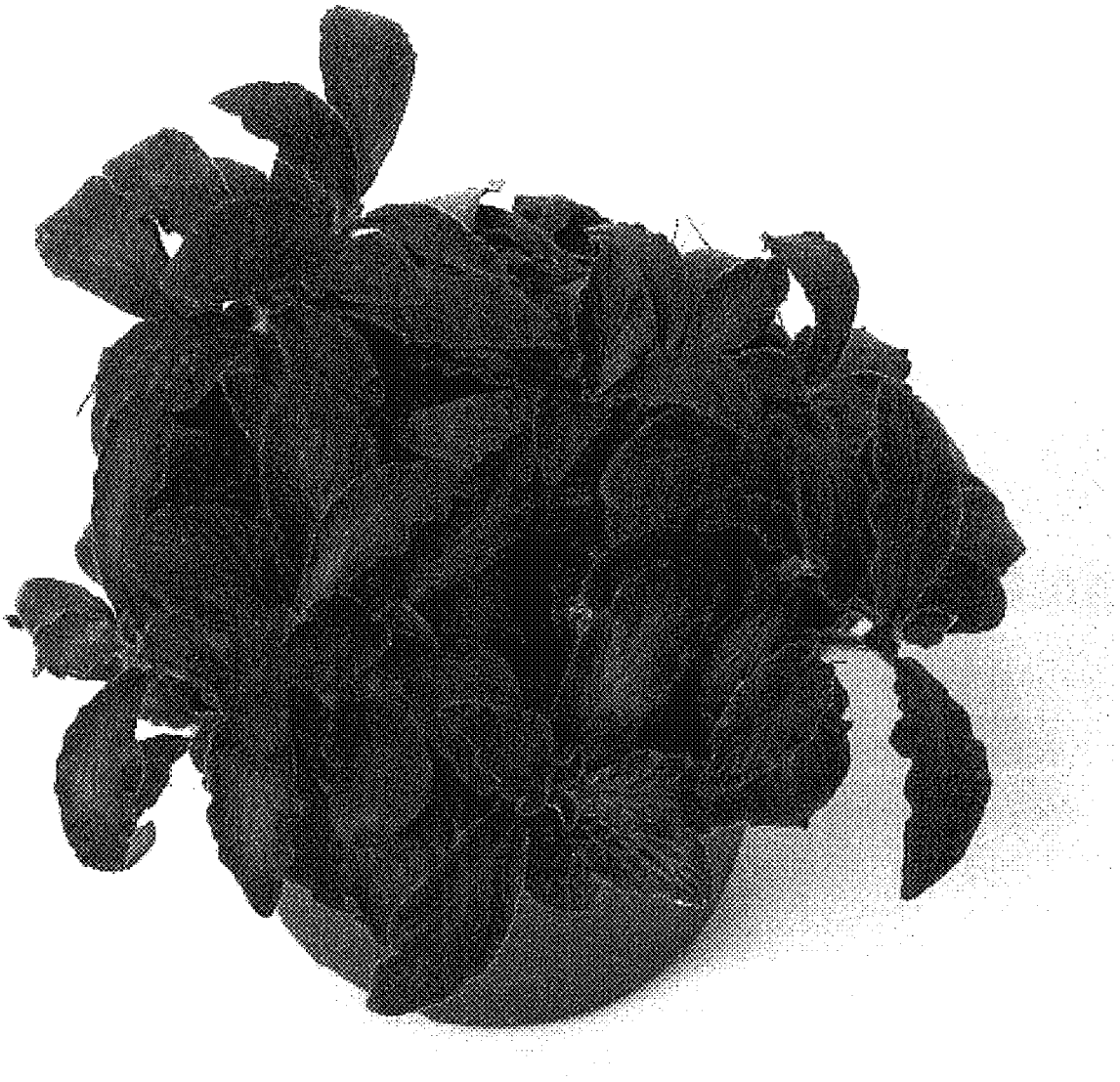

* * * * *